United States Patent [19]

Andrews et al.

[11] Patent Number: 4,708,478
[45] Date of Patent: Nov. 24, 1987

[54] TUBE CELL FOR ATOMIC ABSORPTION SPECTROPHOTOMETRY

[75] Inventors: Arthur S. Andrews, Royston; David S. Widmer, Cambridge, both of England

[73] Assignee: U.S. Philips Corporation, New York, N.Y.

[21] Appl. No.: 926,822

[22] Filed: Nov. 3, 1986

Related U.S. Application Data

[63] Continuation of Ser. No. 634,922, Jul. 26, 1984, abandoned.

[30] Foreign Application Priority Data

Aug. 3, 1983 [GB] United Kingdom ............... 8320949

[51] Int. Cl.⁴ ............................................. G01N 21/74
[52] U.S. Cl. ...................................... 356/244; 356/312
[58] Field of Search ............................... 356/312, 244

[56] References Cited

U.S. PATENT DOCUMENTS

| 4,111,563 | 9/1978 | Tamm | 356/312 |
| 4,202,628 | 5/1980 | Koizumi et al. | 356/312 |
| 4,204,769 | 5/1980 | Lersmacher et al. | 356/312 |
| 4,303,339 | 12/1981 | Gläser et al. | 356/312 |
| 4,537,506 | 8/1985 | Lersmacher et al. | 356/312 |

FOREIGN PATENT DOCUMENTS

| 2381297 | 10/1978 | France | 356/312 |
| 2064500 | 6/1981 | United Kingdom . | |
| 2088582 | 6/1982 | United Kingdom . | |
| 321696 | 11/1970 | U.S.S.R. | 356/312 |

Primary Examiner—F. L. Evans
Attorney, Agent, or Firm—Paul R. Miller

[57] ABSTRACT

A tube cell for flameless atomic absorption spectrophotometry has a transverse cross-section with the portion above a longitudinally extending line midway between the top and bottom of the tube cell having a smaller cross-sectional area than the portion below that line. The tube cell has an elongated aperture formed close to the bottom of the tube cell for inserting a probe or platform carrying a sample to be analyzed. The cross-section of the tube cell is shaped to maximize the size of the probe which can be used, and accordingly, the sample volume, while keeping the total cross-sectional area to a minimum in order to maximize chemical sensitivity. A number of different cross-sectional shapes are described including a triangular cross-section.

28 Claims, 12 Drawing Figures

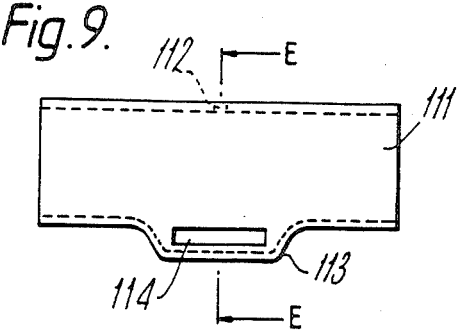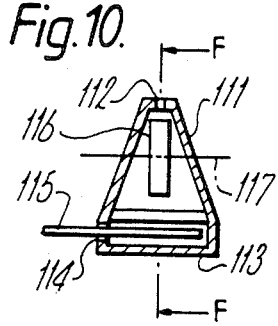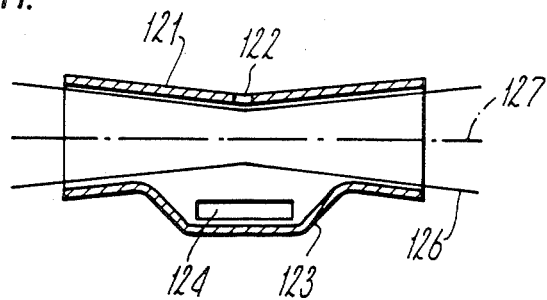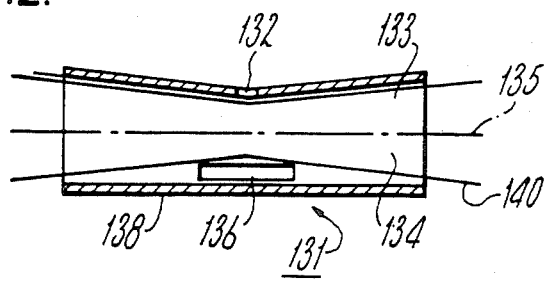

TUBE CELL FOR ATOMIC ABSORPTION SPECTROPHOTOMETRY

This application is a continuation application of previous application, Ser. No. 634,922, filed July 26, 1984, now abandoned and all benefits of such earlier application are hereby claimed for this continuation.

This invention relates to a tube cell for flameless atomic absorption spectrophotometry comprising a tubular body of electrically conductive material with the tubular body being arranged for mounting in a spectrophotometer such that its longitudinal axis is substantially horizontal.

The invention further relates to a tube cell for an atomic absorption spectrophotometer comprising a tubular body of electrically conductive material with the tubular body being arranged for mounting a spectrophotometer such that its longitudinal axis is substantially horizontal and being formed such that when the tubular body is so mounted in a spectrophotometer a pocket extending below the lower wall of the tube and communicating with the interior of the tube is formed midway between the ends of the tube.

Such cells usually comprise a graphite tube which is designed to be mounted between two electrodes for the supply of heating current. The tubes themselves are smooth and normally circularly cylindrical and are usually formed with an opening in the tubular wall in its central region through which a sample to be analysed can be injected. However, tubes having a square cross-section are known from U.K. Pat. No. 1,481,124.

In the flameless atomic absorption spectrophotometry process the graphite tube is heated to a high temperature by the passage of electric current so that the sample substance is first dried and sometimes ashed before reaching a temperature at which it is atomized, i.e. the temperature within the graphite tube at which an atomic cloud is formed in which the individual elements contained in the sample are present in an atomic condition. A beam of radiation, which preferably includes a resonance line of a specific element to be identified in the sample, is passed through the graphite tube along its length so that the proportion of the specific element in the sample can be deduced from the absorption of the beam. The beam of radiation is normally defined as an image of the monochromator entrance slit focussed at the center of the tube. the beam therefore diverges horizontally and vertically in both directions along the tube from the central rectangular image.

When used in this way, the graphite tube serves several functions. First it serves as a carrier for the samples to be analysed; secondly the heating of the graphite tube causes the sample carrier to be evaporated and the sample then to be atomized and finally the tube serves to hold together the atomic cloud thus produced.

The degree of absorption of the beam of radiation and hence the overall sensitivity of the atomic absorption spectrophotometry process is, among other things, a function of the number of free atoms in the path of the beam through the tube cell.

There are a number of factors which make it desirable for the tube cell to have as small a cross-sectional area as possible. These include the power required to raise the temperature of the atomised sample within the radiation beam.

It has been proposed to introduce samples into the tube cells by means of probes as disclosed, for example U.K. Patent Applications Nos. 2,071,845A, 2,088,582A, or platforms as disclosed, for example U.K. Patent Application No. 2,052,788A. The probe or platform remains within the tube cell during measurement. Since the probes/platforms are heated to a very high temperature they will give off visible radiation, as will the tube cell. If this radiation falls on the spectrophotometer detector it will tend to swamp the wanted radiation produced by the radiation beam and make the measurement of the absorption produced by the sample more difficult. It is desirable therefore that the detector is arranged so that radiation from the probe/platform and tube cell does not fall on the detector. If the probe/platform partially interrupts the radiation beam the energy falling on the detector will be reduced and consequently the overall signal to noise ratio will be degraded. To prevent these undesirable effects the probe/platform should be situated as close to the bottom of the tube cell as possible so that the maximum area radiation beam can be used. However, with existing tube cells this either means using small probes/platforms which reduces the maximum sample volume to an undesirably low value or necessitates using larger tube cells with a correspondingly increased power requirement for heating and a lower sensitivity due to the increased volume outside the radiation beam.

It is an object of the invention to enable the provision of tube cells for flameless atomic absorption spectrophotometry in which the problems outlined hereinbefore can be mitigated.

The invention provides a tube cell for flameless atomic absorption spectrophotometry as set forth in the opening paragraph characterised in that the transverse cross-section of the tube is substantially constant along its length or reduces continuously from its ends towards its center and is such that the portion of the cross-sectional area above a line midway between the top and bottom of the tube is smaller than the portion of the cross-sectional area below that line.

The tube cell according to the invention enables a large sample volume to be used while limiting the overall size of the cell to give maximum chemical sensitivity. A dosing aperture may be formed in the upper surface of the tube cell at a point midway between its ends. An elongated aperture may be formed toward the bottom of the tube cell midway between its ends.

The elongated aperture allows a probe carrying a sample to be analysed to be inserted into the tube cell and is located near to the bottom of the tube cell so that the probe lies below the detected ratiation beam. Since the temperature of the tube cell and probe is such that during atomisation and measurement they emit visible radiation, it is desirable that they are out of the detected radiation beam to avoid interference. The cells described and claimed herein may be used in the method and apparatus disclosed in U.K. Patent Application No. 8305745 correspnding to U.S. application Ser. No. 581,484, filed Feb. 17, 1984, provided that the dosing aperture and elongated aperture are provided. It is also possible to dispense with the dosing aperture if the sample is placed on the probe outside the tube cell and inserted into the tube cell on the probe. A platform for containing the sample may be inserted into the tube cell either longitudinally or through the elongated aperture instead of a probe.

The transverse cross-sectional shape of the tube cell may be trapezoidal with the parallel sides extending horizontally.

Alternatively the transverse cross-sectional shape may be triangular with one side on the triangle being substantially horizontal.

These shapes maximize the size of the probe and hence the sample volume possible while making the cross-sectional area of the tube conform closely to the radiation beam.

The tubular body may be flared from a point midway between its ends toward both ends. This enables the tube cell to conform closely to the radiation beam along its entire length.

The tube cell may be formed totally of pyrolytic graphite by means of chemical vapour deposition on a mandrel or spindle.

This enables relatively complex shapes to be produced without requiring machining operations since the shape is defined by that of a mandrel on which the pyrolytic graphite is deposited. Such a process is disclosed in U.K. Patent No. 2,064,500 (corresponding to U.S. patent application Ser. No. 807,114, filed Dec. 10, 1985, which is a continuation of Ser. No. 434,665, filed Oct. 5, 1982, now abandoned, which is a continuation of Ser. No. 211,163, filed Nov. 28, 1980, now abandoned) and which describes coating a pyrolytic graphite deposited from the gas phase onto a spindle of a high-melting point material, with the shape and dimensions of the spindle being such as to correspond to the shape and size of the inner surfaces of the desired crucible, taking into account the heat expansion which occurs during the pyrolytic reactive deposition of the coating, in which the gas pressure, temperature and deposition time of pyrolytic graphite from the gas phase are controlled during the reaction in such a way that the thickness of the pyrolytic graphite coating becomes slightly greater than that required to correspond to the desired outside dimensions and wall thickness of a crucible, the hollow pyrolytic preform thus produced in pyrolytic graphite being brought to the desired outside dimensions and wall thickness by mechanical machining its outer surfaces and a coating of pyrolytic graphite is then additionally deposited to the inner and outer surfaces of the rough crucible thus obtained. One of the essential features of pyrolytic graphite is a marked anisotropy in its physical properties as frequently described in the literature. This anisotropy, which is dictated in turn by a high degree of orientation of the tightly-packed microcrystalline graphitic layer lattice structure, extends to the chemical behavior. A look at a slice of pyrolytic graphite taken parallel to the direction of growth, i.e. in a direction virtually perpenticular to the lamellar layering, clearly shows that the layer, when regarded either along, or against, the direction of growth, looks different from place to place, and is thus non-uniform. It may therefore be expected that some "topographical" variation exists in the properties of the layer connected with this non-uniformity. A coating of pyrolytic graphite is deposited by a method known per se employing the reactive deposition from the gas phase (CVD method) on a cylindrical spindle acting as a substrate, which consists of a high-melting-point material such as tantalum, but preferably of electrical graphite or vitreous carbon with the most highly polished surface possible. The diameter of the substrate spindle used is of such a size that it corresponds to the inside diameter of the crucible to be made, making allowance for the heat expansion occurring at the deposition temperature (about 2000° C.). The thickness of the deposited layer, which may be controlled via the gas pressure and temperature and especially the deposition time within a certain tolerance range, must be adjusted to a value slightly greater than the desired outside diameter of the crucible. Once coating is completed and the whole has cooled to room temperture, the coating may be slid off the substrate. This gives a hollow cylindrical body of pyrolytic graphite with a smooth inner surface, which is further processed as described below to form a rough crucible. The substrate spindle may generally be used again for further coating processes. The hollow pyrolytic graphite cylinder obtained is now procesed further into a rough crucible. It is best cut to length on a lathe using a hard-metal tool for example, a chisel or on a diamond wheel. A fast running grinding machine is best used for grinding to the desired wall thickness. It is usually necessary to make one or more holes in the side of the crucible. This is best done before grinding, using an ordinary drill. After these machining processes the rough crucible is cleaned (e.g. using a degreasing medium in an ultrasonic bath), dried and taken to the pyrolytic graphite coating station. The rough crucible manufactured as described above is now coated with one or more thin layers of pyrolytic graphite in a known way. One method of performing this step in the process is proposed, for instance in German Patent Application No. P2825759.2-52. This post-coating is one essential feature of the invention. It results in the following: all the "reactive centers" on the inner surfaces of the crucible on the substrate side are blocked in the same way as the uncovered active surfaces and centers produced by drilling, cutting and grinding. The crucible is thus given the chemical passivity of the crucible proposed in the German Patent Application referred to above together with its high quality and long useful life. Sealing is brought about by the second or multiple post-coating which also seals off the interlaminary cracks and fissures often present in pyro-graphite items, with their negative effects on the operation and useful lives of the crucibles. The "sealing" results in a layer which is oriented so that the c-axes corresponding to the direction of growth are perpendicular to the base (rough crucible) everywhere. This also means that the electrical resistance of the crucible is increased, especially at the annular terminal areas which also form the contact surfaces for the current flow. The same applies to the heat resistance at the contact surfaces. Both effects are desirable, the first on account of the favorable current-/voltage ratio in the heating power, and the second because it prevents heat flowing away from the crucible. The "sealing" layer also provides additional mechanical rigidity. It is therefore possible to make very thin-walled crucibles which are yet sufficiently stable. The risk of flaking is also virtually eliminated. It is best for the mass production of the hollow bodies and for their subsequent coating to use the hot-wall pyrolysis method taught in German Patent Specification Nos. 1667649 and 1667650, which permits the simultaneous deposition of coatings on a number of substrates. Here, for the sake of uniformity, the coatings should be performed in at least two steps; depending on the coating thickness wanted. This applies at least to the sealing process, while variations in the wall thickness in the production of the preforms may be compensated by subsequent mechanical machining, provided that the wall thicknesses produced when the preforms are made are oversized. It should be noted that the method is not limited solely to precisely cylindrical substrates. Other internal shapes may be made, i.e. ones with conically widening ends or ones widened in steps. All that is necessary is to make the substrate core of two or more separate parts, preferably with a centering pin. Here, undercuts, which would render it impossible to remove the substrate components from the enveloping coating, must be avoided. Accordingly, as known per se, the AAS crucible consists only of pyrolytic graphite, although the pyrolytic graphite preform is again given a sealing coating. The directions of growth of the preform and the sealing are parallel to the outer and antiparallel to the inner cylindrical surface. This not only blocks some increased chemical reactivity of the surface facing the substrate, but also seals off the interlaminar cracks and fissures which nearly always exist or are produced during operation, thus preventing the ingress of any substance under analysis thereinto. This effect of the invention may be taken as the explanation why the improvements in the properties have not been observed in previous uses of curcibles consisting only of pyrographite which have been achieved, for example, in the coating (sealing) of ordinary graphite tubular crucibles with intact thin pyrographite coatings. The latter applies especially to the extraordinarily long useful lives of the crucibles of the present invention. In addition to these features, the multi-coating crucibles of the invention also have electrical, thermal and mechanical advantages. In this connection, the following finding is noteworthy: If pyrolytic graphite is used as a substrate for further coatings, the new coatings grow on the outer, naturally produced final surface of the substrate (of pyrolytic graphite) epitaxially, i.e. the crystalline structure is maintained and generally there is no detectable separation line. This finding applies only to this one surface and only then as long as it is not altered by any process, whether physical, chemical or mechanical. Any gas absorption between the individual coating steps is insignificant, since the gasses are virtually totally desorbed again during the following coating process, i.e. in the pumping and intense heating stages. New layers grow on all other surfaces, especially the inner surface originally bonded to the substrate, normally without epitaxy. (EXAMPLE 1) Deposition was performed using the hot-wall pyrolysis process on a cylindrical graphite spindle 6.1 mm in diameter and with a polished surface in an atmosphere of propane at a total pressure of p=2.3 mbar and a temperature of 2000° C. At the end of the process and after cooling to room temperature, it was possible to draw from the substrate spindle a pyrographite cylinder with the following dimensions: length (1) 6 cm, outside diameter 7.4 mm, inside diameter 6.2 mm, average wall thickness $\delta=6000$ $\mu m$. The properties of this pyrographite cylinder included: specific gravity $\gamma=2.1$ gcm$^{-3}$, resistance over length (1)<0.1 ohm, specific resistance<$10^{-3}$ ohm cm, ultimate tensile stress at an axial load (P)$\geq 52$ kp$\geq 406$ kp/cm$^2$. (EXAMPLE 2) Forty substrate spindles of graphite (electrical graphite) were coated simultaneously in the conditions set out in Example 1 and forty pyrographite cylinders were manufactured in this manner. They were reduced to a length of 2.8 cm by machining on a lathe. A hole 1.5 mm in diameter was then made in the center of the side wall of the cylinder. The rough crucibles with an outside diameter of 7.4 mm and an inside diameter 6.2 mm were machined on a grinding machine to various outside diameters and thus to wall thicknesses from 500 to 100 $\mu m$. The rough crucibles thus made were then subjected to a second coating process during which a sealing pyrographite coating 10 to 40 $\mu m$ thick was applied.

The invention further provides a tube cell as set forth in the second paragraph characterised in that an elongated aperture is located in the pocket.

This arrangement minimizes the volume of the tube cell outside the sample introduction region while still allowing a large sample volume and maintaining the probe below the radiation beam.

A tube cell as set forth in the second paragraph is disclosed in FIG. 1 of U.K. Pat. No. 1564165. The provision of the recess in the tube cell described is for the purpose of reducing the cell temperature in this region so that the atomised sample does not condense on the outer portions of the tube which are conventionally at a lower temperature than the sample insertion zone. Various other measures to achieve this object are also proposed such as varying the thickness of the walls to vary the electrical resistance of the tube cell along its length.

Embodiments of the invention will now be described, by way of example, with reference to the accompanying drawings, in which:

FIG. 9 shows a fifth embodiment of a tube cell according to the invention,

FIG. 10 is a cross-sectional view on line E—E of the tube cell shown in FIG. 9, and FIG. 11 is a cross-sectional view on line F—F of a modified version of the tube cell shown in FIG. 9, and FIG. 12 is a modified version of the tube cell shown in FIG. 11.

Figure 1:
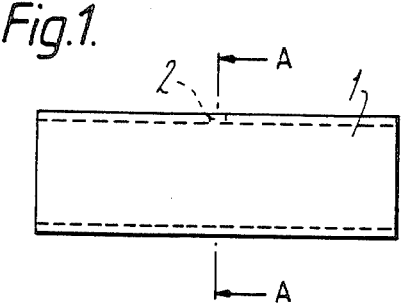
FIG. 1 shows a first embodiment of a tube cell according to the invention.
Figure 2:
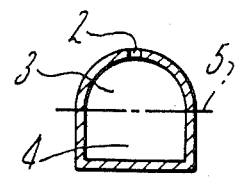
FIG. 2 is a cross-sectional view on line A—A of the tube cell shown in FIG. 1.

As shown in FIGS. 1 and 2 the tube cell comprises a tubular body 1 having a dosing aperture 2 midway between its ends. As can be seen from FIG. 2 the cross-section in a plane transverse to the longitudinal axis of the tube comprises a semicircular upper portion 3 and a rectangular lower portion 4. Thus the cross-sectional area of the upper portion 3 is less than that of the lower portion 4. The boundary between the portions 3 and 4 is defined by an imaginary line 5 located midway between the top and bottom of the tube as viewed in FIG. 2.

Figure 3:
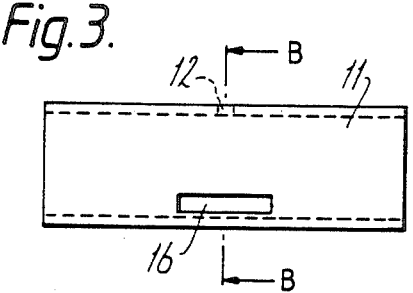
FIG. 3 shows a second embodiment of a tube cell according to the invention.
Figure 4:
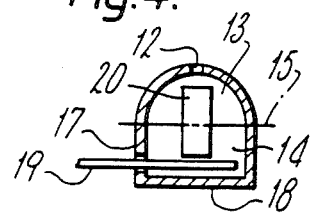
FIG. 4 is a cross-sectional view on line B—B of the tube cell shown in FIG. 3.

FIGS. 3 and 4 show a tube cell similar to that shown in FIGS. 1 and 2 but modified for use with probe or platform sampling. The tube cell comprises a tubular body 11 having a dosing aperture 12 midway between its ends. An elongated aperture 16 is formed in a side wall 17 of the tubular body 11 close to the bottom wall 18. The purpose of the aperture 16 is to allow access to the interior of the tube cell for a probe 19 or for a platform (not shown). In a spectrophotometer the detector is masked so that it sees a radiation beam 20 which is rectangular in section. It is important to ensure that the detector does not see the walls of the tube or the probe since they will emit radiation at the atomising temperature. Consequently the probe 19 should be below the detected radiation beam. With a conventional circular cross-section tube this severely limits the size of sample which may be carried since as the position of the probe within the tube is lowered its depth must be correspondingly reduced since the chord length reduces. This makes it difficult to use probe sampling with small diameter tubes. Increasing the diameter of the tubes allows larger samples to be used but reduces the instrument sensitivity as a larger proportion of the excited atoms is outside the detected radiation beam. The construction shown in FIGS. 3 and 4 overcomes the problem of smaller chordal distances limiting the sample size which can be carried by the probe while not greatly increasing the cross-sectional area of the tube cell.

Figure 5:
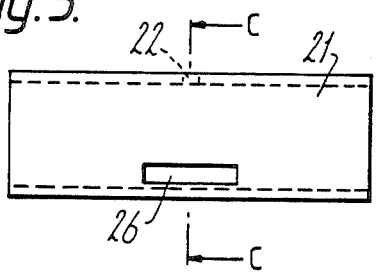
FIG. 5 shows a third embodiment of a tube cell according to the invention.
Figure 6:
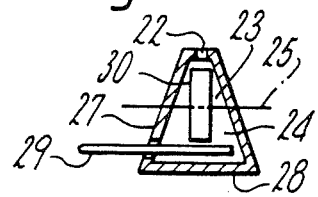
FIG. 6 is a cross-sectional view on line C—C of the tube cell shown in FIG. 5.

FIGS. 5 and 6 show a tube cell comprising a tube cell 21 having a triangular cross-section. A dosing aperture 22 is provided midway between its ends at the apex of the triangle. A longitudinal elongated aperture 26 is provided in one side 27 of the triangle close to the base 28 for inserting the probe 29. As can be seen from FIG. 6 the portion 23 of the cross-sectional area above an imaginary center line 25 is smaller than the portion 24 of the cross-sectional area below that line. This arrangement enables a relatively large sample volume to be placed on the probe within the tube cell while minimizing the cross-sectional area of the cell. Thus a high sensitivity may be achieved with a tube cell as shown in FIGS. 5 and 6.

Various other cross-sectional shapes may be produced which fulfill the condition that the portion of the cross-sectional area above half height is less than that below half height. For example the cell shown in FIGS. 5 and 6 may take a more definitely trapezoidal shape or the side walls may be made concave to more nearly fit the beam shape, care being taken to ensure that this does not unduly restrict the sample size. It should be noted that the sample shoud not be allowed to come into contact with the walls of the tube cell before atomisation when probe sampling is used otherwise the benefits of probe sampling will be lost.

Figure 7:
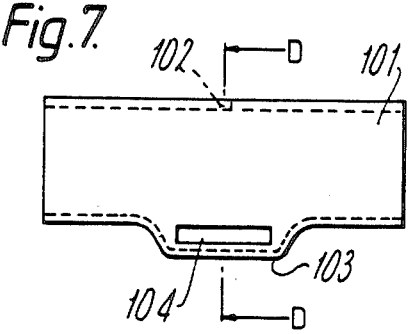
FIG. 7 shows a fourth embodiment of a tube cell according to the invention.
Figure 8:
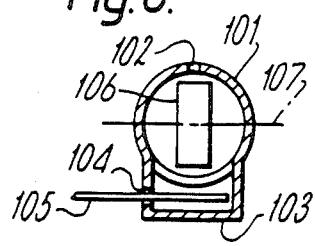
FIG. 8 is a cross-sectional view on line D—D of the tube cell shown in FIG. 7.

FIGS. 7 and 8 show a tube cell which comprises a circularly cylindrical tube 101 having a dosing aperture 102 midway between its ends. A pocket 103 is provided which projects from the bottom of the tube in the region midway between its ends, the pocket containing a longitudinal elongated aperture 104 and communicating with the interior of the tubular body 101. The elongated aperture 104 is provided to enable a probe 105 to be inserted into the pocket 103 where it remains below the radiation beam 106. A line 107 midway between the top and bottom of the tubes and therefore passing through the center of the circular cross-section of the tube separates the cell into two portions and in the region of the sample introduction zone the upper portion is smaller than the lower portion by virtue of the pocket 103 projecting below the general outline of the tubular body.

FIGS. 9 and 10 show a similar arrangement to that shown is FIGS. 7 and 8. The difference being that the tubular body 112 is of triangular cross section rather than circular. Thus this tube cell comprises a tube cell as described with reference to FIGS. 5 and 6 modified by the provision of a pocket 113 in the region of the sample introduction zone. This arrangement enables the radiation beam 116 to occupy a larger proportion of the tube cell cross-section away from the region of the sample introduction zone.

FIG. 11 shows a cross-sectional view on line F—F of FIG. 10 of a modification of the tube cell shown in FIG. 9. The tube cell 121 is flared from its center toward its ends so that the upper and lower walls of the tube cell follow the outline of the radiation beam 126 which is normally brought to a focus midway between the ends of the tube cell. This modification may be made to any of the tube cells shown in FIGS. 1 to 10 and to tube cells of any other cross-sectional shape.

FIG. 12 shows a modification of the tube cell shown in FIG. 11. The tube cell shown in FIG. 12 comprises a tubular body 131 with the upper portion 133 flared toward both ends of the tube from a point midway between its ends. The lower portion 134 is defined by a straight wall 138 and has the same cross-sectional shape and area along the length of the tubular body. An elongated aperture 136 is provided at a point close to the bottom wall 138 of the tubular body and midway between the ends of the tubular body. The radiation beam 140 is brought to a focus at a point midway along the tubular body and by making the bottom wall 138 straight space is created below the radiation beam 140 for the positioning of a probe through the aperture 136.

The tube cells described may be formed from graphite which is machined to shape as is well known for circularly cylindrical tube cells but since the shapes proposed are difficult and expensive to produce by machining it is advantageous to produce the tube cells by a chemical vapour deposition technique, for example as described in U.K. Patent Application No. 2,064,500. The tube cells described with reference to FIGS. 1 to 6 can be produced particularly simply by this method but the remaining tube cells require the use of split mandrels or spindles to enable the deposited tube cells to be removed from the mandrels. Subsequent machining steps may be necessary to produce the dosing and probe insertion apertures.

What is claimed is:

1. A tube cell for an atomic absorption spectrophotometer comprising
   a tubular body of electrically conductive material having a length with a longitudinal axis extending substantially horizontal,
   said tubular body having a cross-section in a plane transverse to said longitudinal axis, said transverse cross-section being at least a minimum at the center of said length of said tubular body, and
   said tubular body having a cross-sectional area for said transverse cross-section above a horizontal line midway between a top and a bottom of said tubular body, said cross-sectional area above said horizontal line being smaller than the cross-sectional area for said transverse cross-section of said tubular body below said horizontal line.

2. A tube cell according to claim 1, wherein said transverse cross-section increases in area from said center toward ends of said tubular body.

3. A tube cell according to claim 1, wherein said transverse cross-section is substantially constant in area along said length of said tubular body.

4. A tube cell according to claim 1, wherein a dosing aperture is formed in an upper surface at said center of said tubular body.

5. A tube cell according to claim 4, wherein an elongated aperture is formed toward said bottom of said tubular body, said elongated aperture being at said center of said tubular body.

6. A tube cell according to claim 4, wherein said transverse cross-section is trapezoidal with parallel sides extending horizontally.

7. A tube cell according to claim 4, wherein said transverse cross-section is triangular with one side of the triangle being substantially horizontal.

8. A tube cell according to claim 4, wherein said tubular body is flared from said center toward both ends.

9. A tube cell according to claim 4, wherein said tubular body is formed totally of pyrolytic graphite by chemical vapor deposition on a mandrel.

10. A tube cell according to claim 1 or claim 2 or claim 3, wherein an elongated aperture is formed toward said bottom of said tubular body, said elongated aperture being at said center of said tubular body.

11. A tube cell according to claim 1 or cliam 2 or claim 3, wherein said transverse cross-section is trapezoidal with parallel sides extending horizontally.

12. A tube cell according to claim 1 or claim 2 or claim 3, wherein said transverse cross-section is triangular with one side of the triangle being substantially horizontal.

13. A tube cell according to claim 1 or claim 2 or claim 3, wherein said tubular body is formed totally of pyrolytic graphite by chemical vapor deposition on a mandrel.

14. A tube cell according to claim 1, wherein a pocket extends below said tubualr member, said pocket communicating with the interior of said tubular body, and said pocket being formed midway between ends of said tubular body, and wherein an elongated aperture is provided in said pocket.

15. A tube cell according to claim 14, wherein a dosing aperture is formed in an upper surface at said center of said tubular body.

16. A tube cell according to claim 15, wherein said transverse cross-section is trapezoidal with parallel sides extending horizontally.

17. A tube cell according to claim 15, wherein said transverse cross-section is triangular with one side of the triangle being substantially horizontal.

18. A tube cell according to claim 15, wherein said tubular body is flared from said center toward both ends.

19. A tube cell according to claim 3, wherein a dosing aperture is formed in an upper surface at said center of said tubular body.

20. A tube cell according to claim 19, wherein an elongated aperture is formed towards said bottom of said tubular body, said elongated aperture being at said center of said tubular body.

21. A tube cell according to claim 19, wherein said transverse cross-section is trapezoidal with parallel sides extending horizontally.

22. A tube cell according to claim 19, wherein said transverse cross-section is triangular with one side of the triangle being substantially horizontal.

23. A tube cell according to claim 19, wherein said tubular body is formed totally of pyrolitic graphite by chemical vapor deposition on a mandrel.

24. A tube cell according to claim 3, wherein a pocket extends below said tubular member, said pocket communicating with the interior of said tubular body, and said pocket being formed midway between ends of said tubular body, and wherein an elongated aperture is provided in said pocket.

25. A tube cell according to claim 24, wherein a dosing aperture is formed in an upper surface at said center of said tubular body.

26. A tube cell according to claim 25, wherein said transverse cross-section is trapezoidal with parallel sides extending horizontally.

27. A tube cell according to claim 25, wherein said transverse cross-section is triangular with one side of the triangle being substantially horizontal.

28. A tube cell for an atomic absorption spectrophotometer comprising
a tubular body of electrically conductive material having a length with a longitudinal axis being substantially horizontal,
a pocket extending below said tubular body, said pocket communicating with the interior of said tubular body, and said pocket being formed midway between ends of said tubular body, and
an elongated aperture in said pocket.

* * * * *